United States Patent [19]  
Krauss et al.

[11] Patent Number: 4,799,389  
[45] Date of Patent: Jan. 24, 1989

[54] TANDEM SAMPLER ACTUATION DEVICE

[75] Inventors: Owen T. Krauss, Dartmouth; Norman G. Gruber, Halifax, both of Canada

[73] Assignee: Western Atlas International, Inc., Houston, Tex.

[21] Appl. No.: 16,335

[22] Filed: Feb. 19, 1987

[51] Int. Cl.⁴ .............................................. G01N 1/16
[52] U.S. Cl. ................................... 73/863.31; 73/151; 73/864.63
[58] Field of Search ................ 73/155, 863.31, 864.63, 73/151

[56] References Cited  
U.S. PATENT DOCUMENTS  
2,111,982  3/1938  Mason, Jr. .................. 73/863.31 X Primary Examiner—Jerry W. Myracle  
Attorney, Agent, or Firm—Barry C. Kane

[57] ABSTRACT

A triggering device for actuating a plurality of serially coupled fluid samplers disposed in a borehole includes a housing having a pair of pistons, each coupled to opposing valves in the tandem fluid samplers. The pistons are locked apart by locking bearing urged against the housing by one of the pistons. Closing of the valve in the upper sampler drives one piston releasing the locking bearing and allowing the other piston to move upwards, thus actuating the lower sampler.

15 Claims, 2 Drawing Sheets

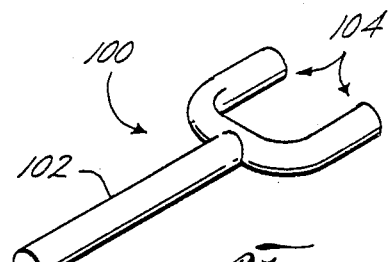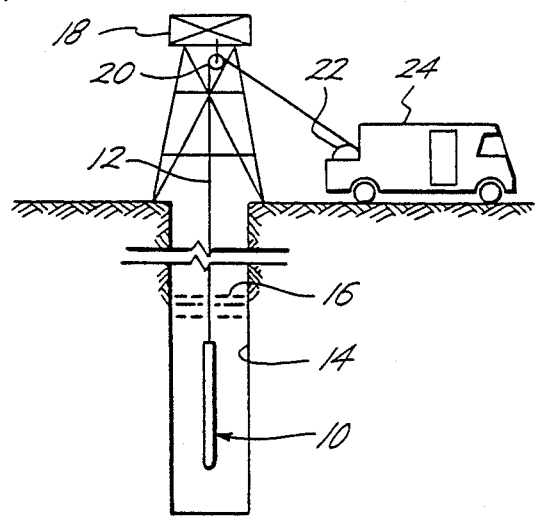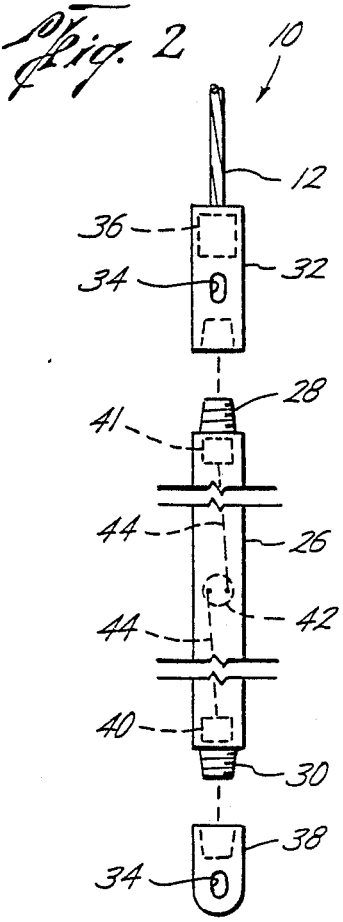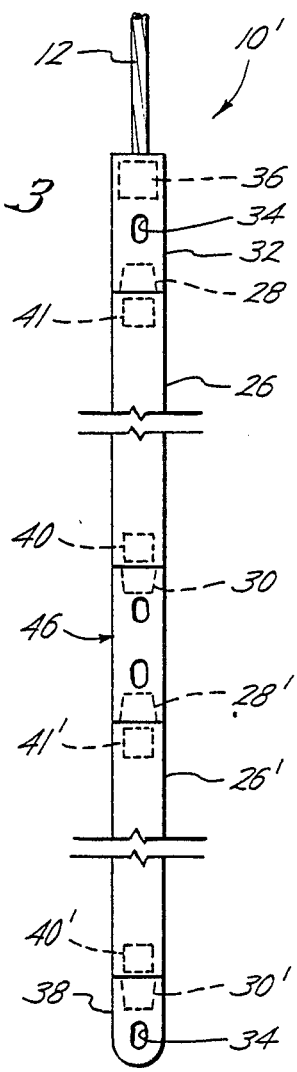

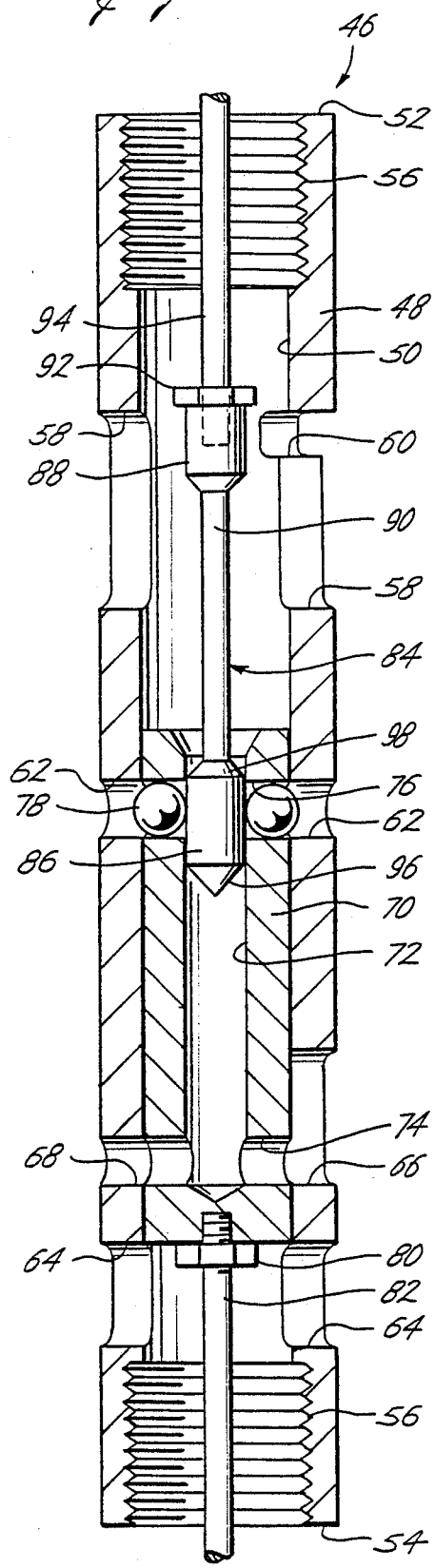
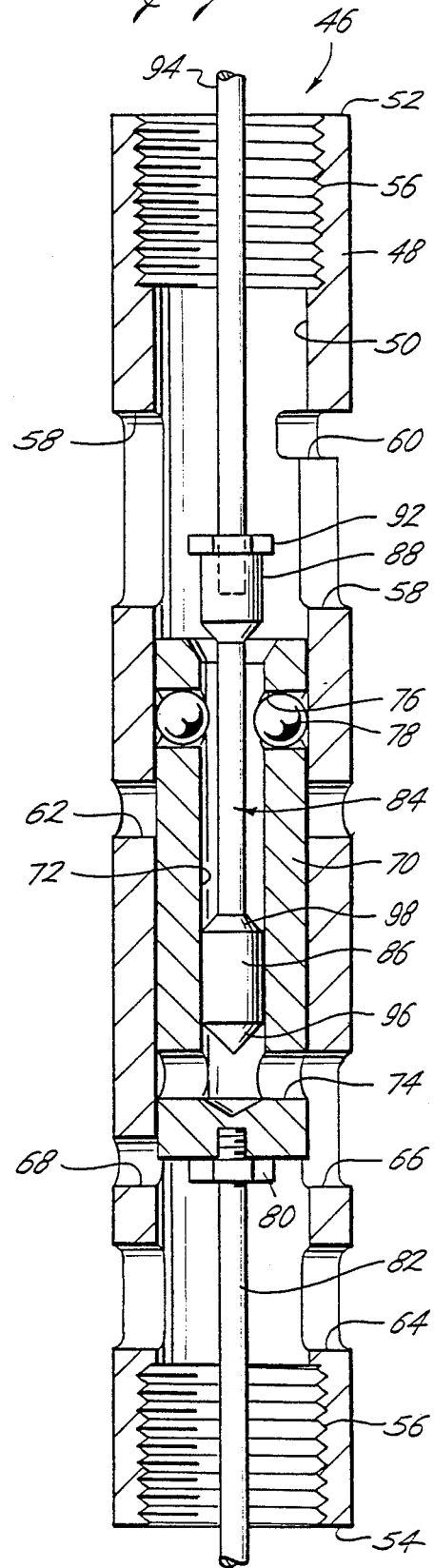

TANDEM SAMPLER ACTUATION DEVICE

BACKGROUND OF THE INVENTION

1. Field of the Invention

This invention relates to fluid samplers and particularly to subsurface samplers used in petroleum exploration.

2. Discussion of the Related Art

In petroleum exploration, it is often desirable to sample fluids within a borehole at particular stages of the drilling, testing or production processes. This is particularly the case when the well bore has entered or passed through a zone of interest within the earth. The fluid samples provide valuable information to the reservoir engineer as to the viability of the well being drilled.

The current design of subsurface samplers have not changed drastically over the past two decades. In general, a typical subsurface sampler consists of a predetermined length of steel tubing having a spring-actuated valve or stopper in each end. Each valve opens inwardly and when closed, forms a tight seal. Both valves are interconnected by a collet mechanism within the sampler tube so that the manual closing of one valve causes the other valve to close. When released, each valve snaps closed driven by the spring on each end.

A motorized triggering mechanism is threaded to the upper end of the sampler tube and is electrically connected via a wireline to a power source at the surface. The electrical trigger holds the valves open until an operator at the surface directs the trigger to release.

It used to be that a single sampler tube was lowered into a borehole to a preselected depth to collect a fluid sample. Because of ever-increasing drilling depths and multiple pay zones, a plurality of samples required a long period of time to complete.

Leutert (North Sea) Ltd. of Aberdeen, Scotland, manufactures a device used to couple two or more of the previously described subsurface samplers in tandem. The coupling device provides a mechanical triggering mechanism dependent upon the upper sampler to close the lower sampler. Reportedly, the Leutert trigger uses the kinetic energy created by the closing action of the lower valve in the upper sampler to drive a retaining ring from around a multi-finger collet. The collet is allowed to open, thereby allowing a rod coupled to the upper valve in the tandemly-coupled, lower sampler to move upwards, thus closing the valves therein. The closing action of the lower valve in the lower sample may in turn drive a second Leutert trigger, actuating a third sampler, and so on.

A major disadvantage of the Leutert triggering device is that it often times does not work. The outward force of the collet upon the retaining ring creates large amounts of friction thus preventing the retaining ring from being moved by the closing of the lower valve in the upper sampler.

A second disadvantage in the Leutert triggering device is a spring which often times prevents the retaining ring from being moved off the collet and thus prevents the collet from opening.

Another disadvantage in the Leutert triggering device is the mechanical complexity of the device which results in increased manufacturing and operating costs.

SUMMARY OF THE INVENTION

It is an object of this invention to provide a tandem actuation device for triggering serially-coupled subsurface samplers.

It is another object of this invention to provide a tandem actuation device having substantially no forces transverse to the longitudinal axis of the device.

It is yet another object of this invention to provide a tandem actuation device having fewer moving parts and is less expensive to manufacture.

It is still another object of this invention to provide a reliable triggering device for serially-coupled subsurface samplers.

The tandem actuation device of this invention can include a housing for interconnecting the ends of the subsurface samplers. An upper valve in a lower sampler engages a cylindrical piston slideably received within the housing and held in place by horizontally-opposing bearings partially received within the housing. A second piston coupled to a lower valve of an upper sampler may be received within the cylindrical piston preventing the bearings from disengaging from the housing. Downward motion of the second piston resulting from the closing of the lower valve in the upper sampler, allows the bearings to disengage from the housing which in turn allows the cylindrical piston to move upwards by the closing of the upper valve in the lower sampler.

In another aspect of this invention, the tandem actuation device may be employed to trigger a single subsurface sampler by coupling a solenoid to the top thereof. An armature within the solenoid may be connected to the second piston. When the solenoid is activated, the armature drives the second piston downward into the cylindrical piston, thus disengaging the bearings and allowing the cylindrical piston to move upwards by the closing action of the upper valve in the sampler.

BRIEF DESCRIPTION OF THE DRAWINGS

A better understanding of the benefits and advantages of our invention may be obtained from the appended detailed description and the drawings, wherein:

FIG. 1 is a general diagram of a subsurface sampler assembly disposed within a borehole;

FIG. 2 is an exploded elevational view of a single subsurface sampler assembly;

FIG. 3 illustrates two subsurface samplers coupled in tandem by this invention;

FIG. 4 is an elevational view in cross section of this invention in the cocked position;

FIG. 5 is an oblique view of a tool that may be used in this invention; and

FIG. 6 is an elevational view in cross section of this invention in the triggered position.

DETAILED DESCRIPTION OF A PREFERRED EMBODIMENT

FIG. 1 is a generalized diagram of a subsurface sampler assembly 10 coupled to one end of a wireline 12 lowered to a preselected depth within a borehole 14 having a fluid 16 therein to be sampled. The subsurface sampler 10 is typically lowered into the borehole 14 via the wireline 12 from a particular structure above the borehole 14 such as a derrick 18. As shown in the Figure, the wireline 12 passes around a pulley 20 and may be connected to a reel 22 aboard a truck 24. An operator within the truck 24 may raise or lower the sampler 10 assembly 10 within the borehole 14 by winding or unwinding wireline 12 from the reel 22. It is understood that the sampler assembly may be used equally as well on an offshore rig where the reel 22 would be mounted on a portable shed.

FIG. 2 is an exploded elevational view of the sampler assembly 10 of FIG. 1. Generally, the sampler assembly 10 has a steel-tubular sampler 26 open at the upper and lower ends, 28 and 30 respectively. The upper or first end 28 is threaded and receives a cross over 32 which in turn is connected to the end of the wireline 12. The cross over 32 is generally cylindrical and has a plurality of slotted ports radially extending therethrough and indicated as 34. A motorized trigger mechanism 36 is affixed above this cross over 32 and is operably connected to an electrical conductor extending internally along the length of the wireline 12. The lower or second end 30 is also threaded and receives a nose cone piece 38 having a plurality of radially spaced ports 34 extending therethrough similar to the upper cross over 32. The nose cone piece 38 acts to round-off the blunt, threaded end of the sampler 26.

The upper and lower ends 28 and 30 of the sampler 26 each have a valve or stopper 40 and 41 slideably disposed therein respectively. The upper and lower valves 40 and 41 are spring loaded and interconnected to an interlock 42 by actuator stems 44. The valves 40 and 41, interlock 42 and actuator stems 44 are shown by dotted lines in the open position. It can be seen from the Figure that when the valves 40 and 41 are opened, they are drawn inside of the sampler 26. It is understood that the valves 40 and 41 close each end of the sampler 26 when the interlock 42 is in the released position.

Refer to FIG. 3 where a tandem sampler assembly 10' is shown in an elevational view. Two samplers 26 and 26' are connected in series by a tandem actuation device (TAD) 46. The TAD 46 is threaded onto the lower end 30 of sampler 26 and an upper end 28' of the second sampler 26'. The upper end 28 of the upper sampler 26 is coupled to the cross over 32 while a lower end 30' of the sampler 26' receives the nose cone piece 38 as originally described in regard to FIG. 2. The lower sampler 26' contains an upper and a lower valve 40' and 41' respectively identical to those described in sampler housing 26.

The distance between the two tandemly-coupled samplers 26 and 26' may be readily changed by altering the length of the TAD 46. It is understood that more than two samplers such as 26 and 26' may be coupled in tandem, each sampler separated from the other by a TAD such as 46.

FIG. 4 is an enlarged elevational view of the TAD 46 in cross section. The TAD 46 includes a housing 48 having a cylindrical inner wall 50. An upper and lower ends 52 and 54, respectively, are open with a predetermined length of the inner wall 50 at each being threaded and indicated as 56. The threaded ends 52 and 54 of the TAD 46 readily couple to either end of the sampler housings such as 26 and 26'.

A plurality of ports transversely extend through the housing 48 at various points along its length. Two rectangular intake ports shown as 58 extend through housing 48 immediately inboard of the threads 56 at the upper end 52 of the TAD 46. Each intake port 58 has a notch 60 milled at the top of one side of the port. Two circular ports shown as 62, having a predetermined diameter such as one-quarter inch, transversely extend through housing 48 midway along its length. Two exhaust ports 64 similar in size to intake ports 58 transversely extend through housing 48 immediately above threads 56 at the lower end 54 of the TAD 46. Between exhaust ports 64 and the circular ports 62 midway along the length of housing 48 are two ports 66 and 68 diametrically opposing each other and are of different shapes and sizes. Port 66 may be an oval slot having its longitudinal axis parallel to that of the housing 48 and is positioned approximately midway between the circular ports 62 and the end 54 of the housing 48. Port 68 may be circular in shape having the same diameter as the width of port 66 and is positioned opposite the end of port 66 nearest the end 54.

Slideably received within housing 48 is a first piston 70, including a cylindrical body, having an axial bore 72 terminating in a lower transaxial bore 74 extending therethrough. The diameter of the lower transaxial bore 74 is equal to the diameter of port 68. An upper transaxial bore 76 passes through and intersects the axial bore 72. The diameter of transaxial bore 76 is larger than that of the circular ports 62 located midway along the housing 48.

Residing within the upper transaxial bore 76 on each side of the axial bore 72 are locking bearings 78. Bearings 78 have substantially the same diameter as the upper transaxial bore 76.

The end of piston 70 not having the axial bore 72 therein, engages and is in intimate contact with a free end 80 of a plunger rod 82 coaxially extending within the end 54 of housing 48. The opposite end of plunger rod 82 is coupled to the upper valve 40' of the lower sampler 26'. With the valve 40' in the open position, the piston 70 is positioned within housing 48 such that the lower transaxial bore 74 is aligned with port 68.

A second piston 84, having a cylindrical head 86 interconnected to a piston foot 88 by a lesser diameter shaft 90, is coupled to a free end 92 of a second plunger rod 94 coaxially extending within the end 52 of housing 48. The opposite end of plunger rod 94 is coupled to the lower valve 41 of the upper sampler 26. With the upper sampler 26 coupled to the TAD 46, the head 86 of piston 84 is slideably received within the axial bore 72 of piston 70. The head 86 of piston 84 has a frusto-conical free end 96 and a tail portion 98 that tapers to the lesser diameter shaft 90. With the lower valve 41 of the upper sampler 26 in the open position, the cylindrical head 86 of piston 84 is positioned adjacent the upper transaxial bore 76 in piston 70.

FIG. 5 is an oblique view of a cocking tool 100 which may be used with this invention. The cocking tool 100 may include a handle 102 having a diameter substantially equal to the diameter of slot 66, bore 68, and the lower transaxial bore 74. One end of handle 102 may be bifurcated into two tines generally indicated as 104. The distance between the tines 104 may be substantially equal to or slightly greater than the diameter of the piston foot 88 of the second piston 84.

In the assembly and operation of the TAD 46, the piston 70 having the locking bearings 78 in the upper transaxial bore 76, is positioned within the housing 48 such that the lower transaxial bore 74 aligns with port 68. The handle portion 102 of cocking tool 100 is inserted through ports 66 and 68 and the transaxial bore 74 temporarily locking piston 70 in place. The second piston 84 is attached to the free end 92 of the plunger rod 94 extending from the lower valve 41 in the upper sampler 26. Housing 48 is threaded onto the lower end 30 of sampler 26 so that the head 86 of piston 84 is slideably received within the axial bore 72 of the piston 70. The frusto-conical end 96 of head 86 forces the locking bearings 78 outwards and partially into ports 62. It should be remembered that the valves 40 and 41 in the upper sampler 26 are held open by the motorized triggering mechanism 36 coupled to the top. The lower sampler 26' may be threaded into the lower end 54 of the TAD 46 such that the free end 80 of plunger rod 82 engages the bottom of piston 70 and holds open valves 40' and 41'. The handle portion 102 of the cocking tool 100 can now be withdrawn from the lower transaxial bore 74 in piston 70. The tandem sampler assembly 10' is lowered into the borehole to the desired depth.

Once the tandem sampler assembly 10' is at the desired depth within the borehole 14, an operator in the truck 24 at the surface directs an electrical current over a conductor contained within the wireline 12 to he tandem sampler assembly 10'. The electrical current received by the motorized trigger mechanism 36 allows the upper valve 40 in the upper sampler 26 to close. The closing action of the upper valve 40 also results in the closing of the lower valve 41, thus driving the second plunger 92 and attached second piston 84 downwards as shown in FIG. 6. The downward movement of the second piston 84 drives the head 86 past the locking bearings 78. The locking bearings 78 are forced inward towards the shaft 90, thus releasing the first piston 70 from the locked position within the housing 48. The first piston 70 is in turn driven upwards by the end 80 of the first plunger rod 82 that is coupled to the upper valve 40' in the lower sampler 26'. The release of the upper valve 40' in the sampler 26' also results in the closing of the lower valve 41' in a manner similar to that previously described. The tandem sampler assembly 10' is returned to the surface where the enclosed fluid samples are taken to the laboratory for analysis.

Occasionally, the tandem sampler assembly 10' is triggered at the surface to insure the function of the TAD 46. The entire device is recocked by using the cocking tool 100. The handle portion 102 of the cocking tool 100 may be inserted into the lower transaxial bore 74 in the piston 70 through slot 66 and drawn downwards until the handle is allowed to extend through bore 68, thus locking the piston 70 in place. The downward motion of the piston 70 forces the plunger rod 82 downwards, interlocking open the valves 40' and 41' in the lower sampler 26'.

The bifurcated end of a second cocking tool 100 may then be inserted through intake ports 58 near the top of the TAD 46 so that the tines 104 of the tool pass on each side of the second piston foot 88 near the free end 92 of second plunger 94. The second piston is pushed upwards causing the second plunger rod 94 to interlock open the lower and upper valves 41 and 40 in the upper sampler 26. The handle portion 102 of the second cocking tool 100 may rest in the notch 60 of the intake port 58 until the motorized trigger mechanism 36 is set to hold the upper valve 40 open. Once the motorized trigger mechanism is set, both cocking tools may be removed and the tandem sample assembly 10' is ready for use.

In an alternate embodiment of this invention, the TAD 46 may have its upper end 52 connected to an electrically- or hydraulically-driven solenoid. The armature of the solenoid may be connected to the piston foot 88 of the second piston 84 previously described. When the solenoid is actuated, the armature may move the second piston 84 downward to release the first piston 70 as previously described, thus triggering the valves in the upper most sampler such as 26 which may in turn triggers others below.

For illustrative purposes, our invention has been described with a certain degree of specificity. Variations will occur to those skilled in the art but which may be included within the scope and spirit of this invention which is limited only by the appended claims.

We claim as our invention:

1. An apparatus to trigger the closing of at least one spring-actuated valve within one end of a sampler, comprising in combination:
    (a) a housing having a plurality of ports extending therethrough coupled to the end of said sampler;
    (b) first means slideably received within said housing for engaging said spring-actuated valve;
    (c) second means axially received by said first means for triggering said first means;
    (d) bearing means disposed within said first means between said housing and said second means for partially engaging at least one of said plurality of ports extending through said housing, releasably locking said first means therein in a first position; and
    (e) means for driving said second means in a first direction within said first means, releasing said bearing means from partially within said at least one of said plurality of ports whereby said spring-actuated valve is allowed to close, driving said first means in a second direction.

2. An apparatus as recited in claim 1 wherein said first means, comprises:
    (a) a first piston having an axial bore and at least one transaxial bore extending therethrough; and
    (b) means coupled to said spring-actuated valve for engaging said first piston.

3. An apparatus as recited in claim 2 wherein said second means, comprises a second piston having a head end and a foot end interconnected by a shaft.

4. An apparatus as recited in claim 3 wherein said bearing means, comprises at least one locking bearing received within said transaxial bore on one side of said axial bore, having a diameter substantially equal to said transaxial bore and greater than said at least one of said plurality of ports extending through said housing.

5. An apparatus as recited in claim 4 wherein said means for driving said second means, comprises
    (a) solenoid; and
    (b) means for coupling said second means.

6. An apparatus as recited in claim 4 wherein said means for driving said second means, comprises'
    (a) a second sampler, having a spring-actuated valve therein, coupled to said housing; and
    (b) a plunger rod interconnecting said valve in said second sampler to said foot end of said second piston.

7. An apparatus as recited in claim 4 wherein said means for engaging said first piston, comprises a second plunger rod having one end coupled to said at least one valve in said sampler and a free end engaging said first piston.

8. A method to trigger the closing of a sampler having at least one spring-actuated valve therein to allow a fluid to enter therethrough, coupled to a tandem actuation device, the method comprising the steps of:
    (a) driving a first piston in a first direction within said tandem actuation device axially into a second piston releasably held within said tandem actuation device;
(b) releasing at least one locking bearing disposed within said second piston between said first piston and partially within a port in a housing of said tandem actuation device; and
(c) allowing said second piston to be driven in a second direction opposite to said first direction within said tandem actuation device by the closing of said spring-actuated valve within said sampler.

9. The method as recited in claim 8 wherein the step of driving said first piston in a first direction, further comprises the steps of:
(a) directing a signal over a wireline coupled to the tandem actuation device;
(b) energizing a solenoid operably connected to said wireline and enclosed within said tandem actuation device, said energizing of said solenoid driving an armature coupled to said first piston in said first direction.

10. The method as recited in claim 8 wherein the step of driving said first piston in a first direction, further comprises the steps of:
(a) actuating triggering mechanism coupled to an upper valve in an upper sampler, interconnected to a lower sampler by said tandem actuation device, said upper valve interconnected to a lower valve by a spring-loaded closing mechanism, so as to close said upper and lower valves in said upper sampler;
(b) driving said first piston, coupled to said lower valve in a first direction, into said second piston, by the closing of said lower valve in said upper sampler.

11. An apparatus to trigger the closing of a lower sampler coupled in tandem to an upper sampler, each sampler having an upper and a lower end retaining an upper and a lower valve, respectively, the apparatus comprising in combination:
(a) a housing having a plurality of ports extending therethrough interconnecting the lower end of said upper sampler to the upper end of said lower sampler;
(b) a first piston axially disposed within said housing and engaging said upper valve in said lower sampler, said first piston having an axial bore and at least one transaxial bore,;
(c) a second piston coupled to said lower valve in said upper sampler received within said housing and axially received within said first piston; and
(d) bearing means disposed within said transaxial bore of said first piston, between said housing and said second piston, for releasably engaging at least one of said plurality of ports extending through said housing with said second piston adjacent thereto.

12. An apparatus as recited in claim 11 wherein said first piston engaging said upper valve in said lower sample, further comprises a plunger rod coupled to said upper valve and urged against said first piston.

13. An apparatus as recited in claim 12 wherein said second piston, comprises:
(a) a head having a frusto-conical first end and a second end tapering inwards;
(b) a foot end interconnected to said lower valve in said upper sampler; and
(c) a shaft interconnecting the inwardly tapering portion of said head and said piston foot.

14. An apparatus for actuating at least one sampler having a tubular casing and a first and a second open-end, an upper and a lower valve disposed within said tubular casing and slideably received within said first and second open-end respectively, bias means disposed within said tubular casing and interconnecting said upper and lower valve for urging said upper and lower valve against said first and second open end, and trigger means coupled to said upper valve in said first sampler for releasably opening said upper and lower valve in said first sampler so as to allow a fluid to enter and exit said first sampler, comprising:
(a) a housing for interconnecting said second open-end of said first sampler to said first open-end of said at least one sampler;
(b) a first piston slideably disposed within said housing and coupled to said upper valve within said at least one sampler;
(c) a second piston slideably received within said first piston and coupled to said lower valve within said first sampler;
(d) means disposed within said first piston between said second piston and said housing for releasably holding said first piston in position with respect to said housing, whereby said first piston is released upon downward motion of said second piston.

15. An apparatus for holding open a lower sampler interconnected in tandem to an upper sampler, each sampler having a first and a second open end, an upper and a lower valve within each sampler and slideably received within said first and second end respectively, biased means disposed within each sampler interconnecting said upper and lower valves and forcing each valve into each respective end, and release means coupled to said upper and lower valve within said upper sampler so as to allow a fluid to pass therethrough, comprising:
(a) means for interconnecting said second end of said upper sampler to said first end of said lower sampler;
(b) a first piston slideably disposed within said means for interconnecting, and engaging to said upper valve in said lower sampler;
(c) a second piston slideably received within said first piston and coupled to said lower valve in said upper sampler; and
(d) means disposed within said first piston, between said second piston and said means for interconnecting, for releasably holding said first piston in position with respect to said means for interconnecting whereby said first piston is released upon downward motion of said second piston.

* * * * *